United States Patent
Tsubota (10) Patent No.: US 8,057,441 B2
(45) Date of Patent: Nov. 15, 2011

(54) CAP FOR DRUG DELIVERY DEVICES

(75) Inventor: Jun Tsubota, Tokyo (JP)

(73) Assignees: Terumo Corporation, Tokyo (JP); Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/687,020

(22) Filed: Mar. 16, 2007

(65) Prior Publication Data

US 2007/0203458 A1    Aug. 30, 2007

Related U.S. Application Data

(63) Continuation of application No. PCT/EP2005/009739, filed on Sep. 10, 2005.

(30) Foreign Application Priority Data

Sep. 24, 2004  (EP) .................................... 04022880

(51) Int. Cl.
*A61M 5/32*    (2006.01)

(52) U.S. Cl. ....................................... 604/198; 604/192

(58) Field of Classification Search .................. 604/198, 604/187, 192; 401/243, 244, 246, 247
See application file for complete search history.

(56) References Cited

U.S. PATENT DOCUMENTS

| | | | | |
|---|---|---|---|---|
| 2,894,300 | A | * | 7/1959 | Treweek ...................... 24/11 P |
| 4,892,428 | A | * | 1/1990 | Grotsch ........................ 401/258 |
| 4,952,088 | A | * | 8/1990 | Groetsch ...................... 401/195 |
| 5,183,469 | A | * | 2/1993 | Capaccio ...................... 604/192 |
| 5,226,895 | A | | 7/1993 | Harris |
| 6,001,089 | A | * | 12/1999 | Burroughs et al. ........... 604/506 |
| 6,221,046 | B1 | | 4/2001 | Burroughs et al. |
| 7,214,212 | B2 | * | 5/2007 | Pommereau et al. ......... 604/192 |
| 2005/0171484 | A1 | * | 8/2005 | Jangula ........................ 604/198 |

FOREIGN PATENT DOCUMENTS

| | | |
|---|---|---|
| EP | 0 518 397 A1 | 12/1992 |
| WO | WO 2005079889 A1 * | 9/2005 |

\* cited by examiner

*Primary Examiner* — Kevin C Sirmons
*Assistant Examiner* — Bradley Osinski
(74) *Attorney, Agent, or Firm* — T. Salmon, Esq.

(57) ABSTRACT

This invention relates to a cap for drug delivery devices, in particular of the injector-type comprising a needle and a needle cover, wherein said cap is suitable as a needle safety tool, by comprising a needle cover retaining portion. In particular, the present invention relates to such devices, which are handled by the patients themselves.

14 Claims, 7 Drawing Sheets

CAP FOR DRUG DELIVERY DEVICES

This application claims priority to European Patent Application 04022880.1, filed Sep. 24, 2004. This application is also a continuation of PCT/EP05/09739, filed Sep. 10, 2005.

This invention relates to a cap for drug delivery devices, in particular of the injector-type comprising a needle and a needle cover, wherein said cap is suitable as a needle safety tool, by comprising a needle cover retaining portion. In particular, the present invention relates to such devices, which are handled by the patients themselves.

BACKGROUND OF THE INVENTION

Drug delivery devices, which are handled by patients themselves and allow individual dosing of the required amount of drug are well known in the art. Generally, such devices have substantially the same purpose as that of an ordinary syringe. A device of the mechanical pen-type is known, e.g., from U.S. Pat. No. 5,226,895.

In such devices, usually a needle assembly comprising a double-ended needle is attached to the device at its distal end. A drug containing cartridge is mounted in a distal end portion of the housing between the needle and a piston rod driving the piston in the cartridge for dispensing the liquid, which is moved by a drive mechanism.

A removable needle cover is mounted on the distal end of the needle to protect the needle from contamination and damage. Further, a removable cap is mounted at the distal end of the housing of the device. The cap is designed to cover and protect the needle and needle cover.

Prior to injection the user (patient, caregiver etc.), must remove the cap from the distal end of the housing and the needle cover from the distal end of the needle. After injection, the needle cover is put back onto the needle and the cap onto the distal end of the housing.

SUMMARY OF THE INVENTION

The problem to be solved by instant invention is to reduce the risk of needle related injuries to the user, which may lead to infection of the user of the above-mentioned kind of drug delivery device. In addition, the present invention serves to avoid the loss of the needle cover during drug delivery and therefore provides improved handling of the drug delivery device.

BRIEF DESCRIPTION OF THE DRAWINGS

FIG. 2 is a side elevation view (2A), a plan view (2B) and a plan view partly in section (2C) showing the needle cover retaining portion of the cap of Example 1.

FIG. 4 is a side elevation view (4A), a side elevation view partly in section (4B) and a distal end view (4C) showing the needle cover retaining portion of the cap of Example 2.

FIG. 6 is a side elevation view (6A), a plan view (6B) and a distal end view (6C) showing the needle cover retaining portion of the cap of Example 3.

DETAILED DESCRIPTION OF THE INVENTION

The present invention provides a cap for a drug delivery device having a needle cover retaining portion, designed to retain a needle cover during injection and to assist in safely attaching/detaching the needle cover from a needle prior to/after injection. Therefore, with the cap of the present invention, a safety tool for retaining a needle cover is provided.

Attaching/detaching a needle cover, e.g. in an axial direction, to/from a needle is achieved by the cap retaining the needle cover by means of the needle cover retaining portion provided on the cap to attach/detach the needle cover.

DEFINITIONS

The term "drug delivery device" according to the instant invention shall mean a single-dose or multi-dose, disposable or re-useable device designed to dispense a selectable or fixed dose of a medicinal product, e.g. insulin, growth hormones, low molecular weight heparins, their analogues and/or derivatives etc. Said device may be of any shape, e.g. compact format or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device shall comprise a needle or a needle assembly. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type, particularly a pen-type injector.

The term "needle" according to the instant invention shall mean a slender hollow instrument designed for introducing material into the body by intravenous, intramuscular, or subcutaneous injection. In particular the term "needle" shall mean a slender hollow instrument having sharp points at both its distal and proximal ends to facilitate its integration with the drug containing cartridge and the injection of the drug into the patient.

The term "proximal end" according to the instant invention shall mean the end of the device or a component of the device, which is furthest away from the dispensing end of the device.

The term "distal end" according to the instant invention shall mean end of the device or a component of the device, which is closest to the dispensing end of the device.

The term "needle cover" according to the instant invention shall mean any component of a drug delivery device designed to protect the needle from physical damage and contamination from environmental factors such as dirt, germs, etc., as well as providing protection for the user of the drug delivery device from needle-stick injuries. Said component can be of any shape and size and manufactured from any suitable material known by a person skilled in the art. In particular, the term "needle cover" shall mean a tubular component of essentially cylindrical shape having a closed distal end and an open proximal end designed to be removably mounted on the distal end of the needle of the drug delivery device.

The tens "cap" according to the instant invention shall mean a component of a drug delivery device designed to cover the needle assembly and needle cover of the device. Said component can be of any shape and size and manufactured from any suitable material known by a person skilled in the art, e.g., suitable plastic. Additionally, the said component is designed to attach, through any suitable means known by a person skilled in the art, to the distal end of the drug delivery device. Furthermore, the component may comprise a clip designed to allow the whole device to be secured in a pocket in the similar way to a pen. In particular, the term "cap" shall mean a tubular component of cylindrical shape having an open proximal end and a closed distal end designed to be removably mounted on the distal end of the drug delivery device and enclose the needle assembly and needle cover of the device.

According to the instant invention the term "needle cover retaining portion" shall mean one or more parts of the cap of a drug delivery device designed to hold a needle cover during injection and assist in the safe attaching/detaching of the needle cover from a needle prior to/after injection. In particular, the term "needle cover retaining portion" shall mean one or more parts of the cap of a drug delivery device designed to hold a needle cover during injection and assist in the safe attaching/detaching of the needle cover from a needle prior to/after injection formed either;

between the cap body of the device and the elastic clip of the cap, or;

in the distal end of the device cap, or;

integrally molded with the cap, or;

molded as a separate part and then attached to the cap body.

According to the instant invention the term "provided on the cap" shall mean that a given functionality, such as needle cover retention or a clip retainer, etc., is present on the cap.

The term "high friction material" according to the instant invention shall mean any material having elastic properties, such as rubber or any other suitable material, that allows it to adapt to the shape and size of the outer surface of the needle cover in order to ensure retention of the needle cover in the needle cover retaining portion through frictional forces during the injection process.

The suitable material may be made of any material that is selected from among various elastic (or soft) materials including, for example, natural rubber, synthetic rubbers such as isoprene rubber, silicone rubber, urethane rubber, styrene-butadiene rubber, fluorinated rubber and acrylic rubber, a porous body of polytetrafluoroethylene, polyamide-, polyester- and otherwise-based thermoplastic elastomers, and porous bodies of polyurethane. Said material can be applied to the inner face of the needle cover retaining portion by adhesion, deposition or the like, or molded integrally with the cap (insert molding, 2-color molding et al.) or molded as a separate part and then attached to the cap by adhesion, fitting or the like. Further the material may be a single piece or a multi-part piece.

EXAMPLES

The following examples describe embodiments of the cap of instant invention, which shall however, not restrict or limit the underlying inventive concept.

Example 1

Figure 1:
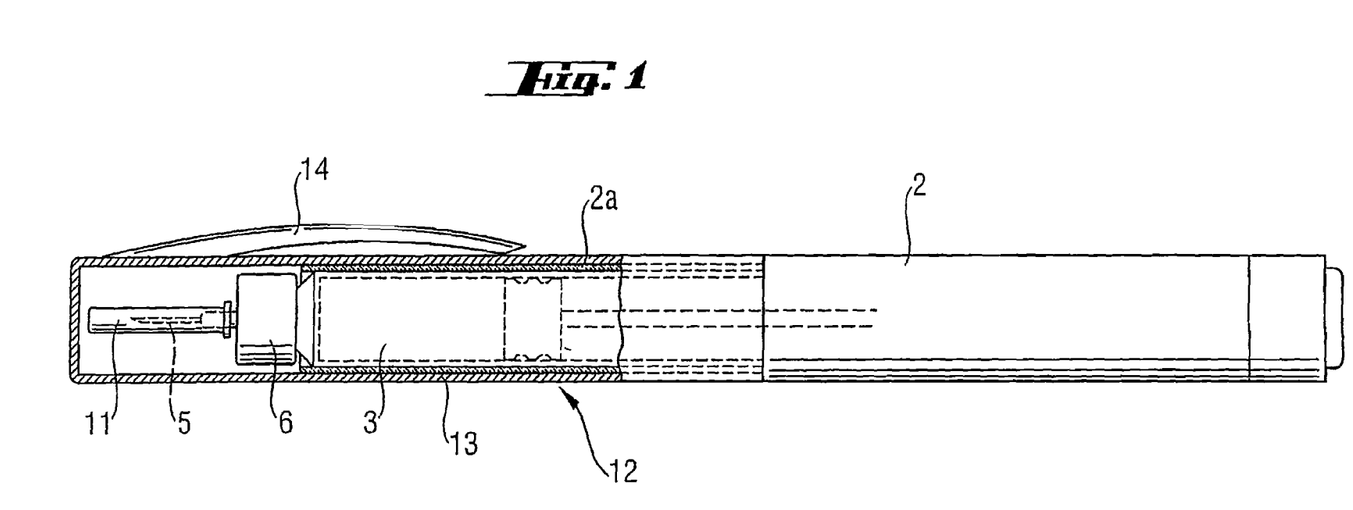
FIG. 1 is a longitudinal sectional side elevation view of an entire pen-type drug delivery device comprising the cap of instant invention.

An outline of the drug delivery device comprising the cap of the invention is described with reference to FIG. 1.

The device shown is of the pen-type and includes a housing 2, a cartridge holding portion 2a coupled integrally and concentrically to the distal end of the housing. A cartridge 3 containing the drug is mounted in the cartridge holding portion 2a. A needle 5 for injection is mounted at the distal end of the cartridge 3 by a needle assembly 6, which is removable.

A removable needle cover 11 covers and protects the needle 5, e.g., from contamination and damage.

An essentially cylindrical cap 12, which is removable, covers the needle assembly 6 including the needle cover 11. The cap 12 includes an essentially cylindrical cap body 13 and an elastic clip 14. Prior to dispensing the drug, the cap 12 and the needle cover 11 are removed.

Figure 2A:
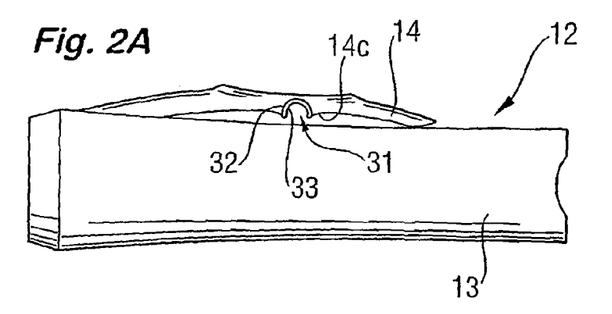
Figure 2B:
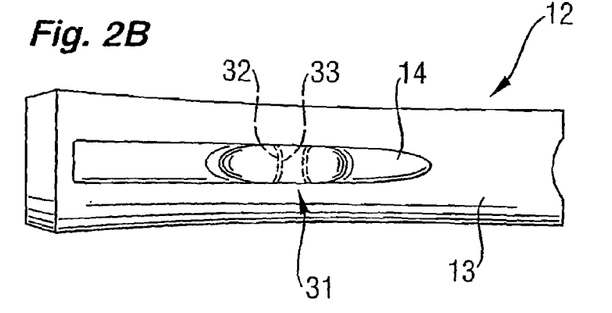
Figure 2C:
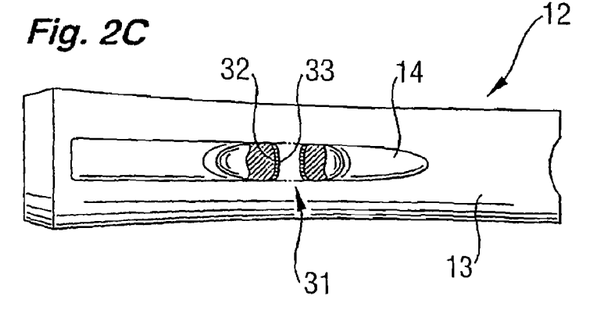
Figure 3:
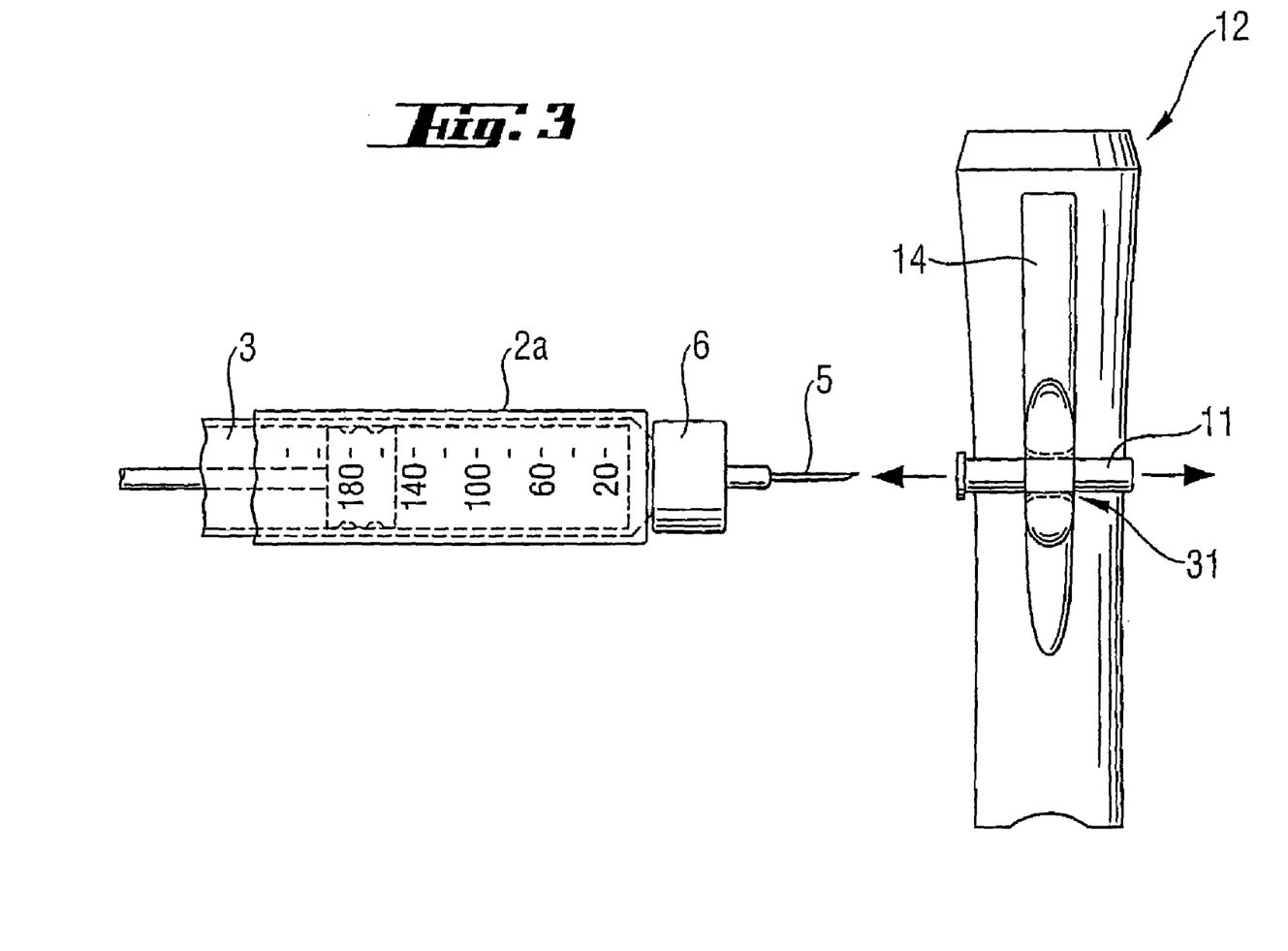
FIG. 3 is a plan view illustrating the operation of attaching/detaching the needle cover from the needle, whilst the needle cover is retained by the needle cover retaining portion of the cap of Example 1.

Details of the needle cover retaining portion 31 are shown in FIGS. 2 to 3. The needle cover retaining portion 31 is formed between the cap body 13 of the cap 12 and the elastic clip 14 of the cap (FIG. 2).

A recessed portion 32 is formed on the inside face 14c of the clip 14. A high friction material 33 is applied by adhesion to the inner face of the recessed portion 32. The high friction material 33 is made from an elastic material such as synthetic rubber. The inner diameter of the high friction material 33 adapts to the outer diameter of the needle cover 11 in order to retain it.

The needle cover retaining portion 31 as shown in FIG. 3, enables the needle cover 11 to be attached/detached to/from the needle 5 safely and easily. When the needle cover 11 is removed from the needle 5, it is retained in the needle cover retaining portion 31 by the tension of the clip 14 of the cap 12. Consequently, the needle cover 11 can be retained safely together with the cap 12 and possible loss of the needle cover 11 can be prevented.

To remove the needle cover 11 from the needle cover retaining portion 31 after injection and when the needle cover 11 has been reattached to the needle 5, the user needs to apply a force to the distal end of the needle cover 11 to overcome the frictional resistance of the high friction material 33.

Example 2

Figure 4A:
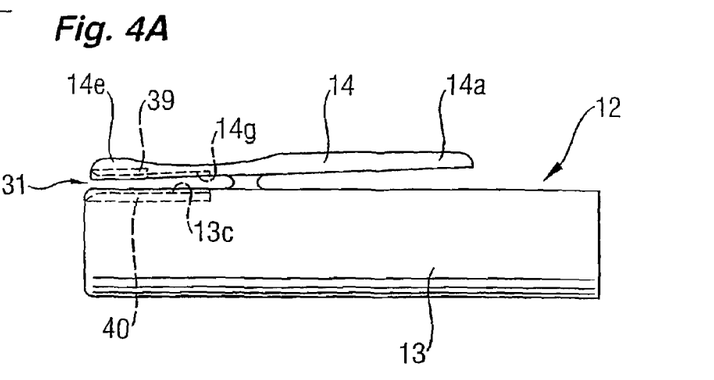
Figure 4B:
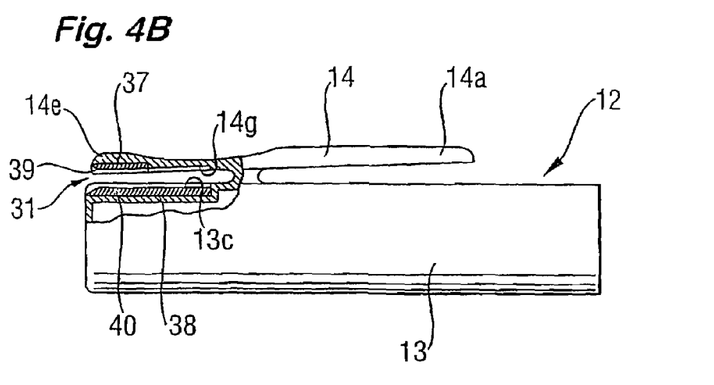
Figure 4C:
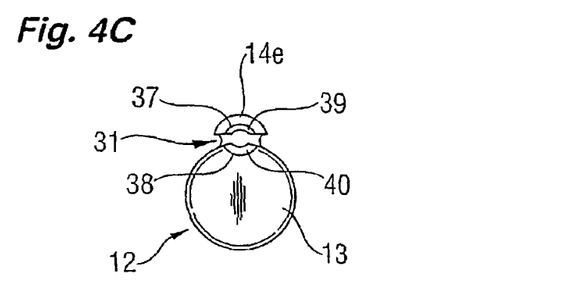
Figure 5:
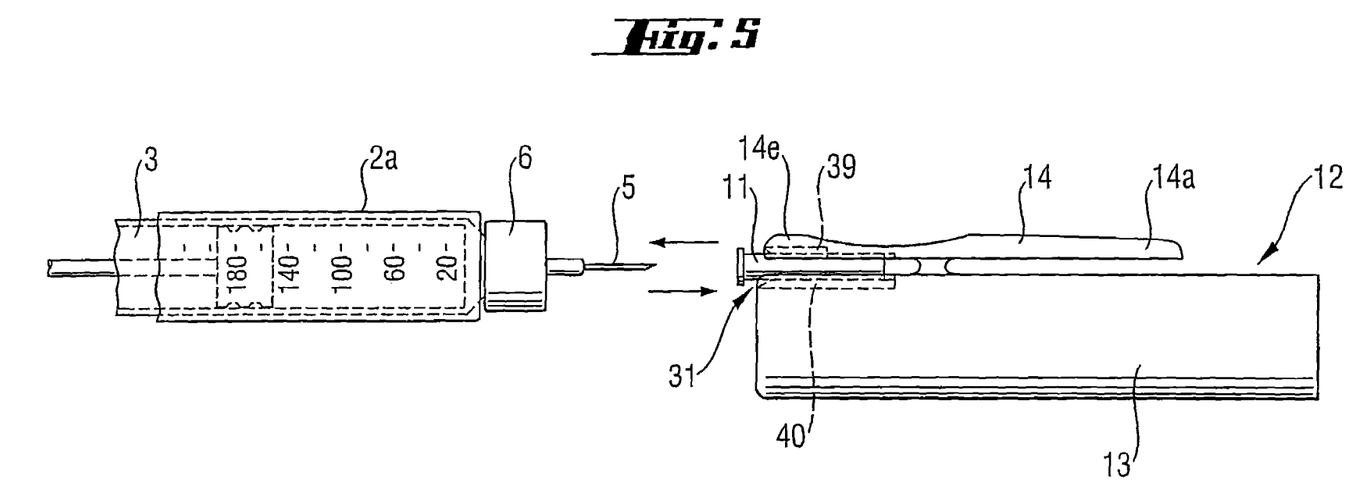
FIG. 5 is a side elevation view illustrating the operation of attaching/detaching the needle cover from the needle, whilst the needle cover is retained by the needle cover retaining portion of the cap of Example 2.

A second embodiment of the cap of the present invention is described in FIGS. 4 to 5.

In this embodiment the needle cover retaining portion 31 is formed along the longitudinal axis of the cap 12 and is located between the cap body 13 and the free end 14e of the clip 14.

The needle cover retaining portion 31 is formed from a pair of upper and lower recessed portions 37 and 38 and a pair of upper and lower elastic high friction materials 39 and 40 (hereinafter referred to simply as "high friction materials"). The high friction materials 39 and 40 are made of synthetic rubber and are applied by adhesion to the inner face of the recessed portions 37 and 38. The recessed portions 37 and 38 are formed on the outer peripheral face 13c of the cap body 13 and an inner face 14g of the free end 14e of the clip 14.

In order to remove the needle cover 11 from the needle cover retaining portion 31 after injection and when the needle cover 11 has been reattached to the needle 5, the user needs to apply a force to the free end 14a of the clip 14 such that the distal free end 14e of the clip 14 is lifted allowing the needle cover 11 to overcome the frictional resistance of the high friction materials 39, 40.

Example 3

Figure 6A:
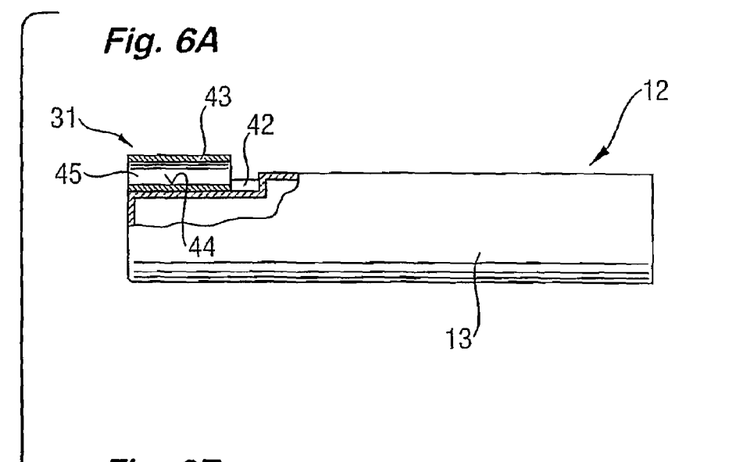
Figure 6B:
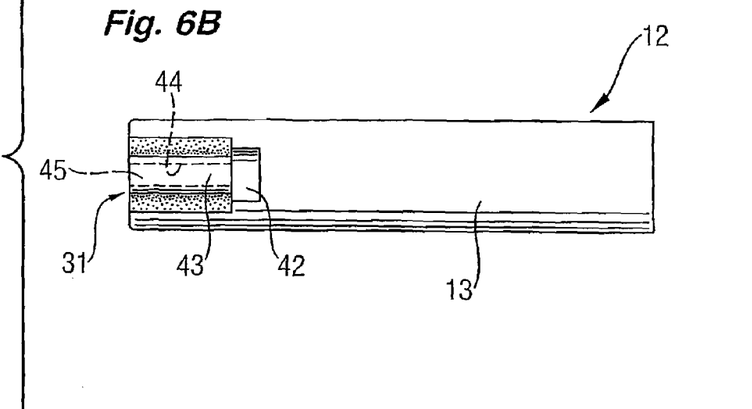
Figure 6C:
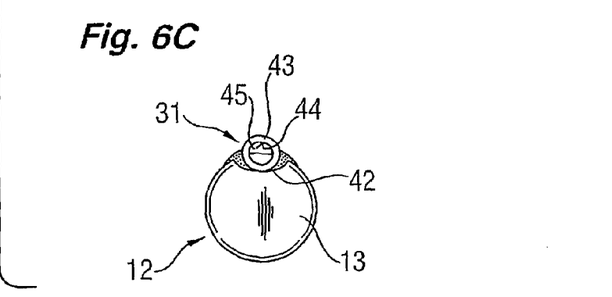
Figure 7:
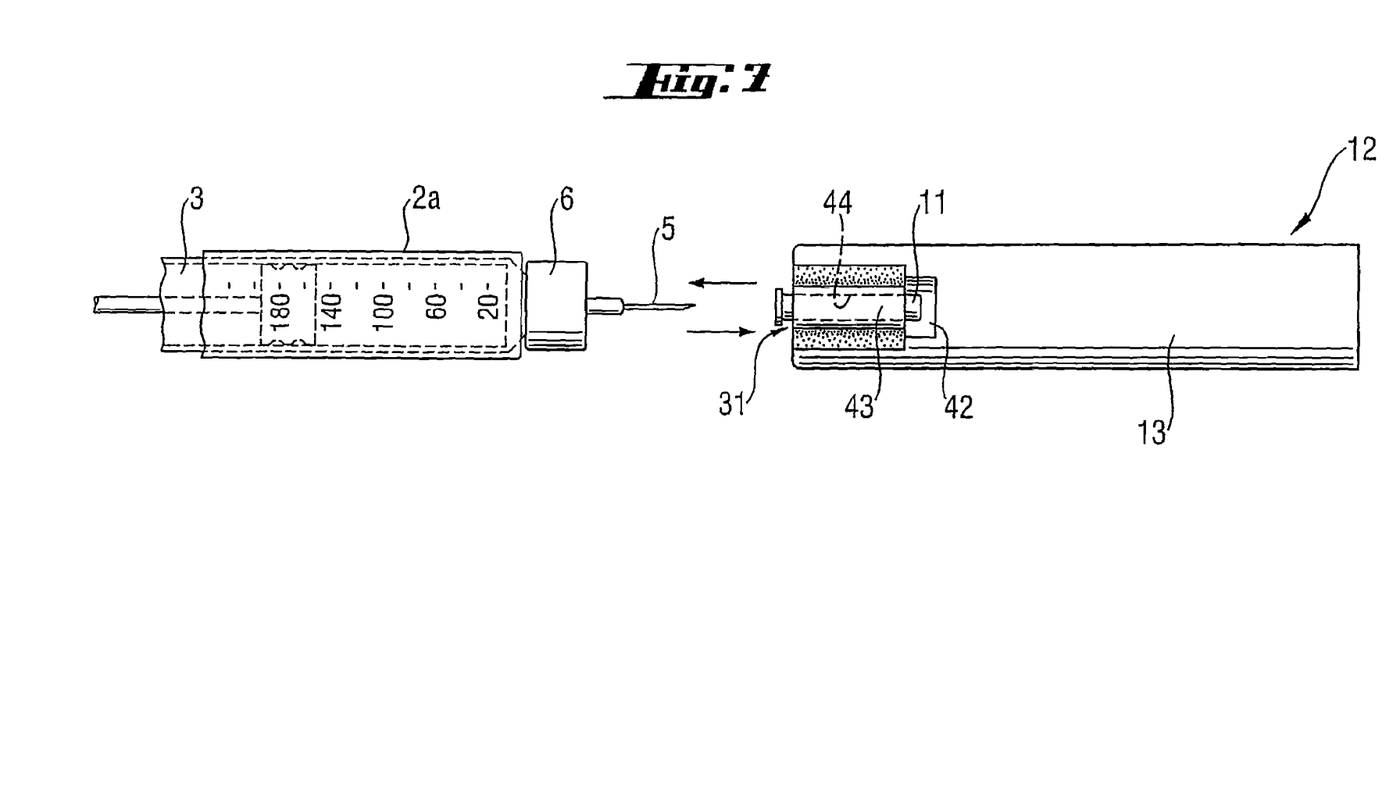
FIG. 7 is a side elevation view illustrating the operation of attaching/detaching the needle cover from the needle, whilst the needle cover is retained by the needle cover retaining portion of the cap of Example 3.

A third embodiment of the cap of the present invention is described in FIGS. 6 to 7.

In this embodiment the needle cover retaining portion 31 is formed on the distal outer peripheral face 13c of the cap body 13 of the cap 12. The needle cover retaining portion 31 is formed from an elastic high friction material 43 (hereinafter referred to simply as "high friction material") made of synthetic rubber, which is either molded integrally with the cap body 13 or molded as a separate part and then attached to the cap body 13 by adhesion.

Accordingly, Example 3 of the needle cover retaining portion 31, describes a further alternative by which the needle cover 11 can be attached/detached safely and easily to/from the needle 5.

The cap for a drug delivery device of the present invention is not restricted to the embodiments described in Examples 1, 2 and 3 above, but various, effective alternatives can be envisaged by the person skilled in the art.

What is claimed is:

1. A cap for a drug delivery device, said drug delivery device including a needle and a needle cover, the needle cover being removably mounted on said delivery device surrounding said needle, said cap comprising:
   an elongated hollow body removably mounted on said drug delivery device so as to surround said needle cover, said hollow body having a longitudinal axis extending lengthwise therealong; and
   a socket mounted on said hollow body, said socket being aligned lengthwise parallel to and offset from said longitudinal axis, said socket being engagable with said needle cover with a friction fit for removably retaining said needle cover in an orientation lengthwise parallel to said longitudinal axis in order to assist in attaching and detaching said needle cover from said drug delivery device.

2. The cap according to claim 1, wherein said socket further comprises an elastic material having a higher coefficient of friction than said hollow body, said elastic material increasing the friction between said socket and said needle cover for retaining said needle cover within said socket.

3. A cap for a drug delivery device, said drug delivery device including a needle and a needle cover, the needle cover being removably mounted on said delivery device surrounding said needle, said cap comprising:
   an elongated hollow body removably mounted on said drug delivery device so as to surround said needle cover, said hollow body having a longitudinal axis extending lengthwise therealong;
   a clip mounted on said hollow body, said clip being aligned parallel to and offset from said longitudinal axis and having a free end portion positioned in spaced relation to an outer surface of said hollow body, said needle cover being received and retained between said free end portion of said clip and said outer surface of said hollow body, said clip having an elongated opposite end portion oppositely disposed from said free end portion and aligned parallel to and offset from said longitudinal axis, said opposite end portion being attached in spaced relation to said outer surface of said hollow body at an attachment point located between said free end portion and said opposite end portion, said free end portion and said opposite end portion being movable about said attachment point such that depressing said opposite end portion toward said outer surface of said hollow body lifts said free end portion away from said outer surface of said hollow body thereby facilitating removal of said needle cover from between said free end portion of said clip and said outer surface of said hollow body.

4. The cap according to claim 3, further comprising an elongated recess in said outer surface of said hollow body, said free end portion of said clip overlying said recess, said recess being aligned parallel to and offset from said longitudinal axis for receiving and retaining said needle cover.

5. The cap according to claim 4, further comprising an elastic material having a coefficient of friction higher than said hollow body, said elastic material being positioned within said elongated recess for retaining said needle cover within said recess.

6. The cap according to claim 3, further comprising an elongated recess in said free end portion of said clip, said recess being positioned between said clip and said outer surface of said hollow body and aligned parallel to and offset from said longitudinal axis for receiving and retaining said needle cover.

7. The cap according to claim 6, further comprising an elastic material having a coefficient of friction higher than said hollow body, said elastic material being positioned within said elongated recess for retaining said needle cover within said recess.

8. The cap according to claim 3, further comprising:
   an elongated first recess in said outer surface of said hollow body, said free end portion of said dip overlying said recess, said recess being aligned parallel to and offset from said longitudinal axis; and
   an elongated second recess in said free end portion of said clip, said second recess being in facing relation with said first recess and aligned parallel to and offset from said longitudinal axis, said first and second recesses cooperating to receive and retain said needle cover between said free end portion of said clip and said outer surface of said hollow body.

9. The cap according to claim 8, further comprising an elastic material having a coefficient of friction higher than said hollow body, said elastic material being positioned within said first and second recesses for retaining said needle cover.

10. A drug delivery device for injecting a drug into a patient, said drug delivery device comprising:
    an elongated housing having a cartridge holding portion positioned at one end thereof;
    a cartridge adapted to hold said drug mounted in said cartridge holding portion;
    a needle mounted on and in fluid communication with said cartridge for injecting said drug into said patient;
    a needle cover removably mounted on said cartridge surrounding said needle;
    an elongated hollow body removably mounted on said one end of said housing so as to surround said needle cover, said hollow body having a longitudinal axis extending lengthwise therealong; and
    a socket mounted on said hollow body, said socket being aligned lengthwise parallel to and offset from said longitudinal axis, said socket being engagable with said needle cover with a friction fit for removably retaining said needle cover in an orientation lengthwise parallel to said longitudinal axis in order to assist in attaching and detaching said needle cover from said cartridge.

11. The drug delivery device according to claim 10, wherein said socket further comprises an elastic material having a higher coefficient of friction than said hollow body, said elastic material increasing the friction between said socket and said needle cover for retaining said needle cover within said socket.

12. A drug delivery device for injecting a drug into a patient, said drug delivery device comprising:

an elongated housing having a cartridge holding portion positioned at one end thereof;

a cartridge adapted to hold said drug mounted in said cartridge holding portion;

a needle mounted on and in fluid communication with said cartridge for injecting said drug into said patient;

a needle cover removably mounted on said cartridge surrounding said needle;

an elongated hollow body removably mounted on said one end of said housing so as to surround said needle cover, said hollow body having a longitudinal axis extending lengthwise therealong;

a clip mounted on said hollow body, said clip being aligned parallel to and offset from said longitudinal axis and having a free end portion positioned in spaced relation to an outer surface of said hollow body, said needle cover being received and retained between said free end portion of said clip and said outer surface of said hollow body, said clip having an elongated opposite end portion oppositely disposed from said free end portion and aligned parallel to and offset from said longitudinal axis, said opposite end portion being attached in spaced relation to said outer surface of said hollow body at an attachment point located between said free end portion and said opposite end portion, said free end portion and said opposite end portion being movable about said attachment point such that depressing said opposite end portion toward said outer surface of said hollow body lifts said free end portion away from said outer surface of said hollow body thereby facilitating removal of said needle cover from between said free end portion of said clip and said outer surface of said hollow body.

13. The drug delivery device according to claim 12, further comprising:

an elongated first recess in said outer surface of said hollow body, said free end portion of said dip overlying said recess, said recess being aligned parallel to and offset from said longitudinal axis; and an elongated second recess in said free end portion of said clip, said second recess being in facing relation with said first recess and aligned with said longitudinal axis, said first and second recesses cooperating to receive and retain said needle cover between said free end portion of said clip and said outer surface of said hollow body.

14. The drug delivery device according to claim 13, further comprising an elastic material having a coefficient of friction higher than said hollow body, said elastic material being positioned within said first and second recesses for retaining said needle cover.

* * * * *